United States Patent [19]
Kato et al.

[11] Patent Number: 5,789,746
[45] Date of Patent: Aug. 4, 1998

[54] LIQUID CHROMATOGRAPH MASS SPECTROMETRY AND LIQUID CHROMATOGRAPH MASS SPECTROMETER

[75] Inventors: Yoshiaki Kato, Mito; Tadao Mimura, Hitachinaka, both of Japan

[73] Assignee: Hitachi, Ltd., Tokyo, Japan

[21] Appl. No.: 886,465

[22] Filed: Jul. 1, 1997

[30] Foreign Application Priority Data

Jul. 9, 1996 [JP] Japan ................................ 8-178770

[51] Int. Cl.$^6$ ............................................. H01J 49/00
[52] U.S. Cl. ...................................................... 250/288
[58] Field of Search ........................ 250/288, 288 A, 250/281, 282

[56] References Cited

U.S. PATENT DOCUMENTS 5,142,144  8/1992  Remo et al. .......................... 250/288

*Primary Examiner*—Kiet T. Nguyen
*Attorney, Agent, or Firm*—Kenyon & Kenyon

[57] ABSTRACT

An eluant is supplied to an analyzer column, a sample solution is supplied through a sample inlet. The analyzer column separates the components of the sample solution. The separated components are eluted by the analyzer column, the eluted components are detected by an eluted component detector, the results of detection provided by the eluted component detector is processed by a data processor to produce a liquid chromatogram having peaks indicating the components of the sample. The components of the sample is supplied through a capillary pipe to an ion source and the ion source ionizes the components of the sample. A mass spectrometer subjects the ions produced by the ion source to mass analysis, an ion detector detects the ions included in a mass spectrum to produce an ion chromatogram having peaks. A time difference between the chromatograms is determined beforehand through an experiment using a standard sample, and the liquid chromatogram is shifted on its time axis by the time difference.

12 Claims, 3 Drawing Sheets

UV CHROMATOGRAM

STANDARD SAMPLE SUPPLY SIGNAL

LIQUID CHROMATOGRAPH MASS SPECTROMETRY AND LIQUID CHROMATOGRAPH MASS SPECTROMETER

BACKGROUND OF THE INVENTION

1. Field of the Invention

The present invention relates to a liquid chromatograph mass spectrometry and a liquid chromatograph mass spectrometer. More specifically, the present invention relates to a liquid chromatograph mass spectrometry and a liquid chromatograph mass spectrometer which display a liquid chromatogram and a total ion chromatogram (abbreviated to "TIC") on a screen.

2. Description of the Prior Art

A liquid chromatograph mass spectrometry has prevalently been used in recent years as an effective method of analyzing hard-to-volatilize organic compounds and unstable-to-heat organic compounds.

Liquid chromatography introduces a sample prepared by dissolving a substance in a liquid into an analytical column filled with a packing, and supplies a solvent as a moving phase into the analytical column to separate and detect the components of the sample by the agency of the mutual actions of the sample, the packing and the moving phase. A UV detector (ultraviolet detector) using an ultraviolet ray absorption spectrum among various detectors is prevalently used. Data provided by a data processor is shown in a chart or displayed in a liquid chromatogram on the screen of a CRT. Although the UV detector is highly sensitive, the UV spectrum provided by the UV detector does not necessarily contain sufficient information on the structure of the measured components. Accordingly, a mass spectrometer is used in combination with a liquid chromatographic apparatus to obtain more specific information on the dissolved components.

The mass spectrometer ionizes the components of a sample and provides a mass spectrum. Information on the molecular weights and the chemical structures of the components can be obtained from the mass spectrum. Another chromatogram different from the liquid chromatogram can be produced by integrating the quantities of ions in a specified range of mass. Such a method is called a TIC. A TIC is a chromatogram including information on the components which could be ionized and detected and hence can be matched off against the mass spectrum in one-to-one correspondence. A liquid chromatograph mass spectrometer (abbreviated to "LC/MS") has prevalently been used because the TIC matches off directly against the mass spectrum. The comparison of a TIC with an ordinary liquid chromatogram has become necessary with the recent diffusion of the LC/MS. Accordingly, it has become widespread to measure a TIC signal provided by a UV detector, i.e., a most generally used detector for detecting a liquid chromatogram, and a TIC signal provided by a mass spectrometer simultaneously, and to display the two chromatograms on a screen for comparison, which is disclosed in Japanese Patent Laid-open No. 4-132153.

If the flow rate and the consumption of a moving phase for liquid chromatography are high, much moving phase, which, in most cases, is an injurious substance, such as methanol or acetonitrile, is diffused in the environment to contaminate the environment. Therefore, an analyzer column of a small diameter is used to suppress the consumption of the moving phase (injurious solvent). However, if the diameter of the analyzer column is reduced the moving speed of the eluant decreases accordingly, and the time necessary for the eluant to flow through the UV detector and a capillary pipe to an ion source increases The dead volumes of the UV detector and the capillary pipe affect the development of the chromatograms greatly. The retardation of development of the chromatogram may be avoided by reducing the dead volumes of the UV detector and the capillary pipe. However, there is a limit to the reduction of the dead volumes of the UV detector and the capillary pipe. The smaller the volume of the UV detector is made, the less the UV detector is sensitive. A capillary pipe having a small inside diameter is liable to be clogged. If the capillary pipe is clogged frequently, the analysis is interrupted frequently to change the capillary pipe. The dead volume of the capillary can be reduced by reducing the length instead of reducing the inside diameter. If a conductive liquid, such as an aqueous solution containing an acid or a salt, is supplied through the capillary pipe, leakage occurs through the conductive liquid, the potential of the extremity of the capillary cannot be maintained and stable ionization cannot be achieved. Therefore, the discrepancy between the UV chromatogram and the TIC still remains.

If two components appear successively on the UV chromatogram and only one component appears on the TIC, it is difficult to decide intuitively which component is ionized. If a component indicated by a large absorption on the UV chromatogram is not ionized and a component indicated by a small peak at the foot of the large peak is ionized, a mistake is made in considering that the component indicated by the large peak on the UV chromatogram is ionized. Such discrepancy between the chromatograms tends to cause serious misunderstanding and mistake.

SUMMARY OF THE INVENTION

Accordingly, it is an object of the present invention to provide a liquid chromatograph mass spectrometry and a liquid chromatograph mass spectrometer capable of preventing a mistake or misunderstanding in the relation between a liquid chromatogram and an ion chromatogram when comparing and examining the liquid chromatogram and the ion chromatogram displayed on a screen.

According to the present invention, a liquid chromatograph mass spectrometry comprises producing a liquid chromatogram of components of a sample eluted by an analyzer column included in a liquid chromatograph mass spectrometer by detecting the components of the sample by an eluted component detector, separating ions produced by ionizing the eluted components of the sample by mass for detection, and producing a TIC of the eluted components. The liquid chromatogram and the TIC are displayed simultaneously on a screen, and the liquid chromatogram is shifted on its time axis by a time difference between the liquid chromatogram and the TIC.

DESCRIPTION OF THE PREFERRED EMBODIMENTS

Figure 1:
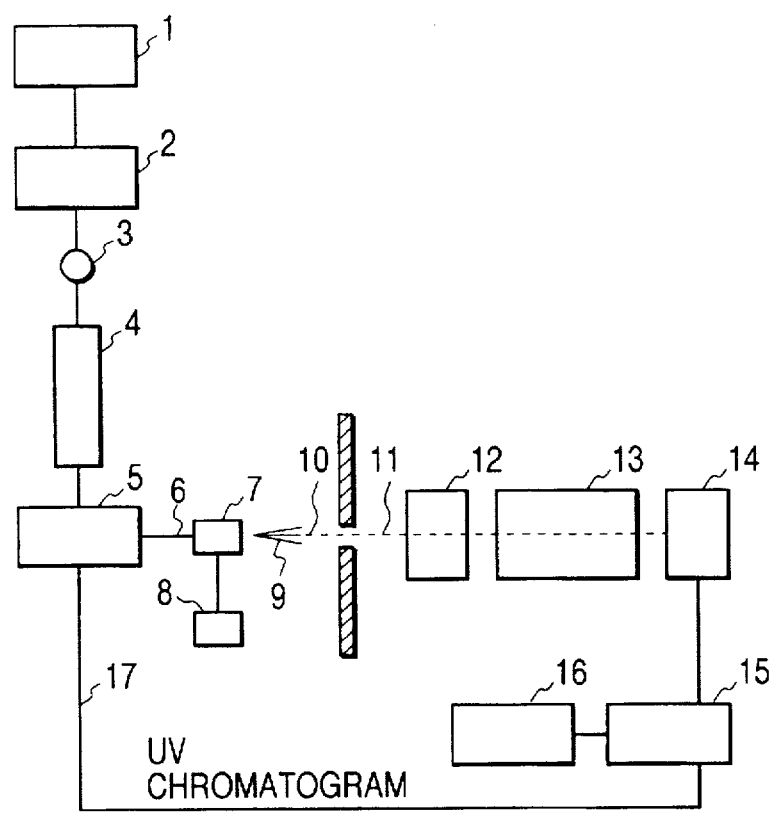
FIG. 1 is a block diagram of a liquid chromatograph mass spectrometer in a first embodiment according to the present invention.

Referring to FIG. 1 showing a liquid chromatograph mass spectrometer in a first embodiment according to the present invention, a pump 2 pumps an eluant 1, i.e., a moving phase, to supply the eluant 1 through a sample inlet 3 into an analyzer column 4. A sample solution is supplied through the sample inlet 3 into the analyzer column 4, and the analyzer column 4 separates the components of the sample solution. The separated components eluted by the eluant 1, i.e., a moving phase, flow together with the eluant 1 from the analyzer column 4 into a UV detector (eluate detector) 5. The components that absorb UV rays are detected. The UV detector 5 sends the results of detection through a UV chromatograph signal line 17 to a data processor 15. The components that absorb UV rays form peaks on a UV chromatogram (liquid chromatogram). The components of the sample and the eluant 1 are sent through a capillary pipe 6 to an ion source unit.

If an ion source is an electrospray ionizer (ESI), a high-voltage source 8 applies a high voltage V in the range of 3 to 4 kV to the tip of the capillary pipe 6, so that the sample solution is sprayed in minute charged liquid particles 9 into the atmosphere. Usually, the capillary pipe 6 is 0.1 mm in inside diameter and about 1 m in length. The minute charged liquid particles collide repeatedly with molecules of the atmosphere and molecules of the solvent are gasified. Consequently, the liquid particles are reduced to finer liquid particles and, eventually, the liquid particles are reduced to ions 11. The ions 11 are sampled through an aperture 10 and are sent through an ion transfer unit 12 to a mass spectrometer 13. The sample ions are subject to mass spectrometry, and an ion detector 14 detects the ions. Data provided by the ion detector 14 is processed by the data processor 15 to produce a mass spectrum. Ion currents in the mass spectrum are integrated and quantities of ions are plotted on a time axis to obtain a total ion chromatogram (TIC).

The flow rate of the eluant 1 is about 1 ml/min if the inside diameter of the analyzer column 4 is 3 mm or above. If the eluant 1 flows at that flow rate through the analyzer column 4 of that inside diameter, the eluant 1 is consumed at about 500 ml/day. It is undesirable to discharge such a large quantity of the noxious, harmful eluant, such as methanol or acetonitrile, into the environment. Therefore, in most cases, an analyzer column of 1 mm or 2 mm in inside diameter are used and the flow rate of the moving phase is regulated at about 100 μl/min to reduce the consumption of the harmful solvent to about 50 ml/day.

The general UV detector has a dead volume of about 10 μl. A limit to the volume of the UV detector is in the range of 10 to 5 μl. The capillary pipe 6 is 0.1 mm in inside diameter and about 1 m in length. Therefore, the dead volume of the capillary pipe 6 is 0.00785 ml. Suppose that the moving phase flows through the capillary pipe 6 at a flow rate of 100 μl/min. Then, the moving phase takes a time of (10+7.85)/100=0.1785 min=10.71 s to pass through the capillary pipe 6; that is, the sample passes through the capillary pipe 6 and reaches the mass spectrometer 13 about 10 s after being detected by the UV detector 5. Consequently, the TIC delays by a delay time of about 10 s behind the UV chromatogram. Since the TIC delays by the delay time behind the UV chromatogram, and the UV chromatogram and the TIC are produced on the basis of entirely different principles, respectively, it is very complex to compare the UV chromatogram and the TIC.

Figure 2:
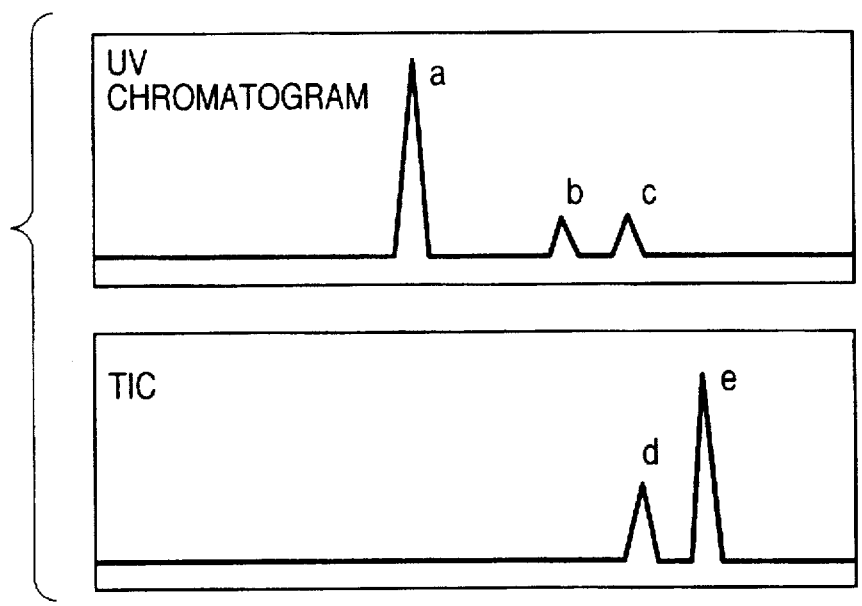
FIG. 2 is a diagrammatic view of assistance in explaining the difference between a liquid chromatogram and a TIC.

For example, as shown in FIG. 2, if the ion source of the mass spectrometer 13 is in capable of ionize a huge component corresponding to a peak a in the UV chromatogram, no signal indicating the huge component appears on the TIC. Even if peaks b and c indicating small components appear successively on the UV chromatogram, the ion source of the mass spectrometer 13, in some cases, ionizes those components at different ionization efficiencies, and it some times occurs that the small component indicated by the peak c on the UV chromatogram is indicated by a large peak e on the TIC.

Figure 3:
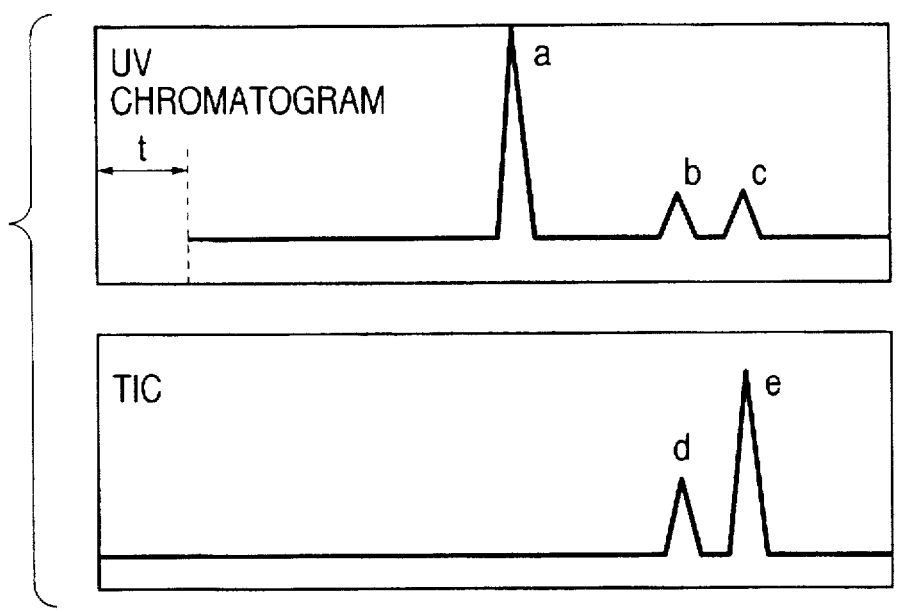
FIG. 3 is a diagrammatic view of assistance in explaining a liquid chromatogram and a TIC produced by a liquid chromatograph mass spectrometry according to the present invention.

The UV chromatogram and the TIC are collected by the data processor 15 and are displayed on the CRT 16. As shown in FIG. 3, the time difference t between the UV chromatogram and the TIC is added to the horizontal axis, i.e., the time axis, of the UV chromatogram when displaying the UV chromatogram on the CRT 16. Consequently, the peaks b and c indicating the components on the UV chromatogram are displayed apparently at the same time as the peaks d and e indicating the same components on the TIC. Therefore, it is quite obvious that the components indicated by the peaks b and c on the UV chromatogram corresponds to those indicated by the peaks d and e on the TIC.

The time difference between the UV chromatogram and the TIC may be measured beforehand by experiments using a known standard sample and the time difference may be stored beforehand in the data processor 15. If it is known beforehand that the component indicated by the peak b on the UV chromatogram is the same as that indicated by the peak d on the TIC in FIG. 3, it is possible to determine the time difference by indicating that the component indicated by the peak b on the UV chromatogram is the same as that indicated by the peak d on the TIC with a cursor or the like on the CRT 16.

Figure 4:
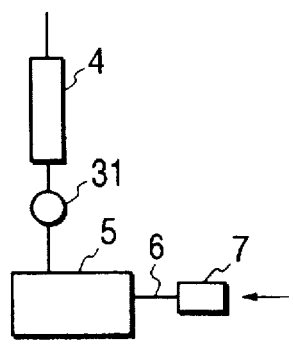
FIG. 4 is a block diagram of an essential portion of a liquid chromatograph mass spectrometer in a second embodiment according to the present invention.

FIG. 4 shows an essential portion of a liquid chromatograph mass spectrometer in a second embodiment according to the present invention, in which parts like or corresponding to those shown in FIG. 1 are designated by the same reference characters. A sample inlet 31 is disposed between an analyzer column 4 and a UV detector 5. A pump 2 supplies a moving phase 1 all over the system. A sample has not yet supplied through the sample inlet 31. A standard sample which can be detected by both a UV detector 5 and a mass spectrometer 13, such as ammonium acetate or coumarin, is supplied through the sample inlet 31 into the liquid chromatograph mass spectrometer. The UV detector 5 detects the components of the sample immediately, and the mass spectrometer 13 detects the components of the sample a time t after the detection of the components by the UV detector 5. The time t is stored as a time difference between a UV chromatogram and a TIC in a data processor 15. When displaying the UV chromatogram on a CRT 16 or a chart, the UV chromatogram is shifted by the time t on the time axis thereof.

Figure 5:
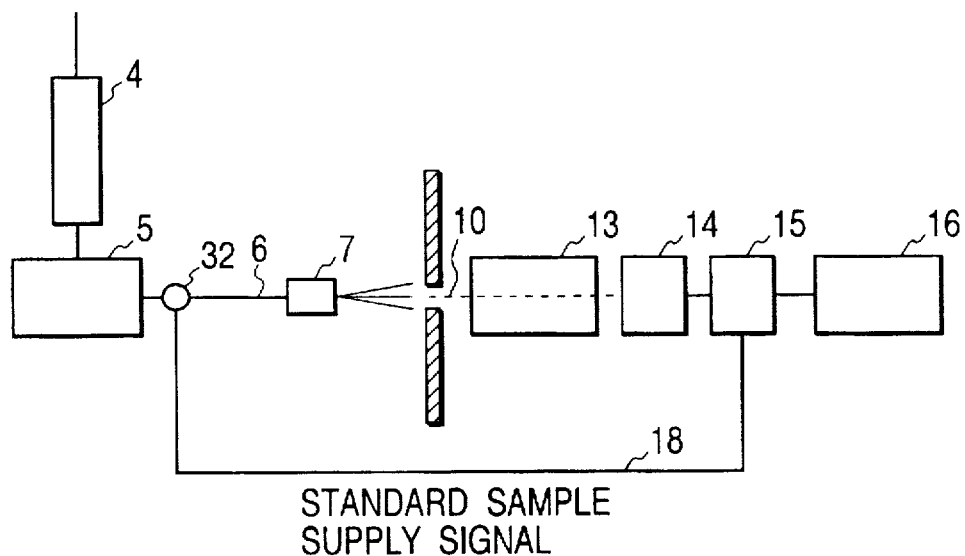
FIG. 5 is a block diagram of a liquid chromatograph mass spectrometer in a third embodiment according to the present invention.

FIG. 5 shows a liquid chromatograph mass spectrometer in a third embodiment according to the present invention. When a standard sample is injected through a sample inlet 32 into the liquid chromatograph mass spectrometer, the sample inlet 32 sends a sample injection signal indicating the reception of the sample through a sample injection signal line 18 to a data processor 15. The data processor 15 measures a time t between the reception of the sample injection signal and a moment when an ion detector 14 detects the standard sample, i.e., a time difference between a UV chromatogram and a TIC. In this case, UV detection may be omitted. When UV detection is omitted, the standard sample may be any suitable substance provided that the same can be ionized by an ion source and whether or not the standard sample is capable of absorbing UV rays is not important. The sample inlet 32 may be disposed either above or below the UV detector 5.

Figure 6:
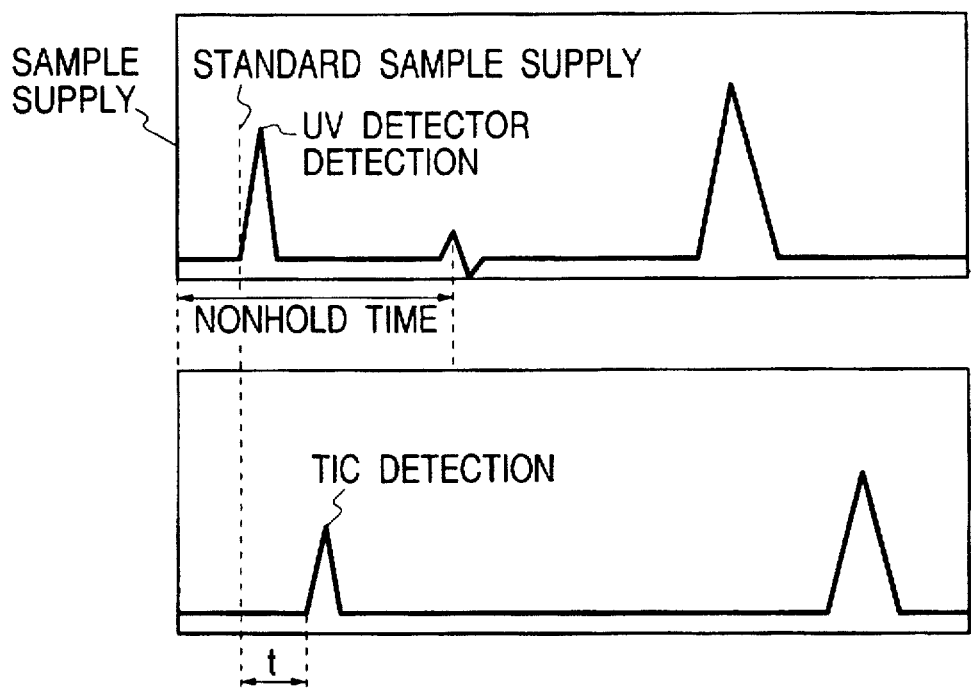
FIG. 6 is a diagrammatic view of assistance in explaining the relation between a liquid chromatogram and a TIC.

FIG. 6 is a diagrammatic view of assistance in explaining the relation between a liquid chromatogram and a TIC. The interruption of analysis to measure the time difference t between chromatograms is not desirable from the viewpoint of carrying out analysis efficiently. In actual liquid chromatographic analysis, there is a time period subsequent to the start of analysis in which the components of a sample never appear. Time will not be wasted if this time period is used for measuring the time difference t. This time period subsequent to the start of analysis in which the sample does not appear corresponds to a nonhold time between a moment when the sample is injected into the liquid chromatograph mass spectrometer and a moment when a component which is not held at all by the analyzer column appears. When a moving phase is supplied at a flow rate of 100 μl/min to an analyzer column of 1 mm in inside diameter and 30 cm in length, the components of the sample is not eluted for about 2.4 min. The standard sample is injected through the sample inlet 31 into the liquid chromatograph mass spectrometer and the time difference t is measured during the nonhold time of about 2.4 min. The time difference t can surely be measured in a nonhold time of 2 min because the time difference t is about 10 s.

The operator is able to recognize the correspondence between the peaks on the UV chromatogram and those on the TIC without being conscious of the time difference between the UV chromatogram and the TIC, and hence the erroneous recognition and misinterpretation of the peaks can be avoided. The time difference can be measured at any optional time if a simple inlet is disposed below the analyzer column. The time difference can accurately be measured and time for analysis is not wasted if the time difference is measured during the nonhold time of the analyzer column.

As is apparent from the foregoing description, according to the present invention, the liquid chromatograph mass spectrometer prevents the erroneous recognition and misinterpretation of the peaks in the liquid chromatogram and the ion chromatogram when both the liquid chromatogram and the ion chromatogram are displayed on the screen of a display for comparative examination.

What is claimed is:

1. A liquid chromatograph mass spectrometry comprising: producing a liquid chromatogram of components of a sample eluted by an analyzer column included in a liquid chromatograph mass spectrometer by detecting the components of the sample by an eluted component detector; separating ions produced by ionizing the eluted components of the sample by mass for detection; and producing a total ion chromatogram of the eluted components by an ion detector; wherein the liquid chromatogram and the total ion chromatogram are displayed simultaneously on a display, and the liquid chromatogram is shifted relative to the total ion chromatogram on its time axis so as to adjust a time difference between the liquid chromatogram and the total ion chromatogram.

2. The liquid chromatograph mass spectrometry according to claim 1, wherein a standard sample detected by both the eluted component detector and the ion detector is received at a position between the analyzer column and the eluted component detector, the difference between the respective positions of the liquid chromatogram and the total ion chromatogram is adjusted by a time difference between the respective times of detection of the standard sample by the eluted component detector and the ion detector.

3. The liquid chromatograph mass spectrometry according to claim 2, wherein the standard sample is received automatically.

4. The liquid chromatograph mass spectrometry according to claim 2, wherein the standard sample is received before the eluted component detector detects the components of the sample.

5. The liquid chromatograph mass spectrometry according to claim 1, wherein a standard sample detected by the ion detector is received at a position between the analyzer column and the eluted component detector, a time period between the reception of the standard sample and the detection of the standard sample by the ion detector is used as the time difference.

6. The liquid chromatograph mass spectrometry according to claim 1, wherein a standard sample detected by the ion detector is received at a position immediately below the eluted component detector, the difference between the respective positions of the liquid-chromatogram and the total ion chromatogram is adjusted by a time period between the reception of the standard sample and the detection of the standard sample by the ion detector.

7. A liquid chromatograph mass spectrometer comprising: a mass separator having an eluted component detector for detecting components of a sample eluted by a liquid-chromatographic analyzer column, producing a liquid chromatogram from the output of the eluted component detector, and separating ions produced by ionizing the eluted components of the sample by mass; an ion detector for detecting the separated ions to produce an ion chromatogram; and a display displaying the liquid chromatogram and the ion chromatogram simultaneously thereon; wherein the liquid chromatogram is shifted relative to the ion chromatogram on its time axis to adjust a time difference between the liquid chromatogram and the ion chromatogram when displaying the liquid chromatogram and the ion chromatogram on the display.

8. The liquid chromatograph mass spectrometer according to claim 7, further comprising: a sample inlet disposed between the analyzer column and the eluted component detector; and a data processor for determining a time difference between time when the eluted component detector detects a standard sample detected by both the eluted component detector and the ion detector and time when the ion detector detects the standard sample; wherein the time difference between the liquid chromatogram and the ion chromatogram is adjusted by the time difference determined by the data processor.

9. The liquid chromatograph mass spectrometer according to claim 8 further comprising a standard sample receiving means automatically receiving the standard sample.

10. The liquid chromatograph mass spectrometer according to claim 8, wherein the standard sample is received before the eluted component detector detects the components of the sample.

11. The liquid chromatograph mass spectrometer according to claim 7 further comprising: a sample inlet disposed between the analyzer column and the eluted component detector; and a time determining means for determining a time period between time when a standard sample detected by the ion detector is supplied through the sample inlet and time when the ion detector detects the standard sample; wherein the time difference between the liquid chromatogram and the ion chromatogram is adjusted by the time period determined by the time determining means.

12. The liquid chromatograph mass spectrometer according to claim 7 further comprising: a sample inlet disposed immediately below the eluted component detector; and a time determining means for determining a time period between time when a standard sample detected by the ion detector is supplied through the sample inlet and time when the ion detector detects the standard sample; wherein the time difference between the liquid chromatogram and the ion chromatogram is adjusted by the time period determined by the time determining means.

* * * * *